United States Patent [19]

Green

[11] 4,415,112

[45] Nov. 15, 1983

[54] SURGICAL STAPLING ASSEMBLY HAVING RESILIENTLY MOUNTED ANVIL

[75] Inventor: David T. Green, Norwalk, Conn.

[73] Assignee: United States Surgical Corporation, Norwalk, Conn.

[21] Appl. No.: 315,448

[22] Filed: Oct. 27, 1981

[51] Int. Cl.³ .............................................. A61B 17/04
[52] U.S. Cl. ................................. 227/19; 128/334 R; 227/155; 227/DIG. 1
[58] Field of Search ............... 128/303 R, 325, 334 R; 227/19, DIG. 1, 154, 155

[56] References Cited

U.S. PATENT DOCUMENTS

| | | | |
|---|---|---|---|
| 1,506,073 | 8/1924 | Maynard | 227/155 |
| 3,489,330 | 1/1970 | Mallina et al. | 227/DIG. 1 |
| 3,494,533 | 2/1970 | Green et al. | 227/DIG. 1 |
| 3,499,591 | 3/1970 | Green | 227/DIG. 1 |
| 4,304,236 | 12/1981 | Conta et al. | 227/19 X |

*Primary Examiner*—Paul A. Bell

*Attorney, Agent, or Firm*—Robert M. Shaw; John E. Nathan

[57] ABSTRACT

A surgical stapling assembly including a resiliently mounted anvil member and a staple holding assembly containing a plurality of surgical staples and mounted relative to the anvil member for movement into substantially parallel spaced relation thereto to clamp tissue inserted between the anvil member and staple holding assembly for stapling. If the surgical stapling assembly is overloaded with tissue and clamped, the clamping force results in a displacement of the anvil member relative to the staple holding assembly in the general direction of the clamping force. The amount of displacement of the anvil member permitted by the resilient means is large enough to prevent excessive pressure on the tissue, but not so large that the anvil member is no longer sufficiently close to the staple holding assembly to perform its function of crimping the ends of the staples driven from the staple holding assembly.

10 Claims, 4 Drawing Figures

SURGICAL STAPLING ASSEMBLY HAVING RESILIENTLY MOUNTED ANVIL

BACKGROUND OF THE INVENTION

This invention relates to surgical stapling assemblies. More particularly, the invention relates to a surgical stapling assembly including a resiliently mounted anvil member and a staple holding assembly for use with an actuator assembly to produce an array of crimped surgical staples in body tissue.

Surgical stapling assemblies have been developed in which a staple holding assembly containing a plurality of surgical staples is pivotally mounted relative to an anvil member. The surgical stapling assembly may be manufactured as an integral part of a surgical stapler, which also includes an actuator assembly, or the stapling assembly may be designed and manufactured as a disposable unit for use in a reusable actuator assembly. Representative of such disposable surgical stapling assemblies and reusable actuator assemblies are those disclosed in copending, commonly assigned, U.S. patent applications Ser. No. 188,691, filed Sept. 29, 1980, now U.S. Pat. No. 4,354,628 and Ser. No. 267,080, filed May 26, 1981 now U.S. Pat. No. 4,383,634. Reference is made to these applications only to show a possible environment for the present invention. The subject matter disclosed in these applications is neither essential for adequate disclosure of the present invention nor essential to support the present claims.

Typically in such surgical stapling assemblies, when the staple holding assembly is pivoted toward the anvil member to clamp tissue inserted therebetween in preparation for stapling, opposing surfaces of the staple holding assembly and the anvil member are spaced apart by a predetermined distance which is fixed by the design of the surgical stapling assembly. This spacing is sometimes referred to herein as the "tissue gap" of the stapling assembly and such stapling assemblies are sometimes referred to herein as being of the "fixed tissue gap type."

Because the tissue gap in this type of stapling assembly is fixed, the operator of an instrument comprising an actuator assembly and the surgical stapling assembly must make sure that he or she does not overload the tissue gap by placing more tissue in the stapling assembly than the tissue gap is designed to contain. Most operators will be unable to clamp the tissue when the stapling assembly is overloaded. But some particularly strong operators may not only ignore the increased resistance to clamping which signals overloading, but may actually be able to clamp the overloaded tissue. In that event, the pressure on the overloaded tissue resulting from the increased clamping force and the fixed tissue gap may be greater than it should be and injury to the overloaded tissue may result.

In view of the foregoing, it is an object of this invention to reduce the chance of injury to the tissue being clamped due to an error in the operator's judgment regarding the correct amount of tissue to be placed in surgical stapling assemblies of the type mentioned above.

It is another object of this invention to reduce the possibility of excessive pressure being applied to tissue in surgical stapling assemblies of the type mentioned above when the stapling assembly is overloaded.

SUMMARY OF THE INVENTION

These and other objects of the invention are accomplished in accordance with the principles of the invention by mounting the anvil member on resilient means so that if the surgical stapling assembly is overloaded and the overloaded tissue clamped, the clamping force will result in a displacement of the anvil member away from the staple holding assembly and in the general direction of application of the clamping force, thereby resulting in an increase in the tissue gap and thus reducing the chance of injury to the tissue. The amount of displacement of the anvil member relative to the staple holding assembly permitted by the resilient means is large enough to prevent excessive pressure on the tissue, but not so large that the anvil member is no longer sufficiently close to the staple holding assembly to perform its function of crimping the ends of the staples driven from the staple holding assembly.

Further features of the invention, its nature and various advantages will be more apparent from the accompanying drawings and the following description of the preferred embodiments.

DESCRIPTION OF THE PREFERRED EMBODIMENTS

Although the principles of the invention are applicable to other similar types of surgical stapling apparatus, the invention will be clearly understood from an explanation of its application to a fixed tissue gap type of surgical stapling assembly in which the staple holding assembly is pivotally mounted adjacent one end of the anvil support member for pivotal movement into substantially parallel spaced relation to the anvil member, as shown in the embodiments of FIGS. 1 through 4.

Figure 1:
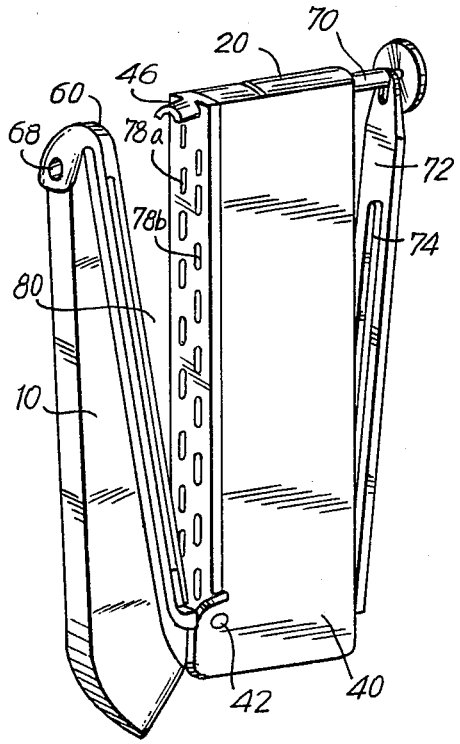
FIG. 1 is a perspective view of an exemplary surgical stapling assembly constructed in accordance with the present invention.
Figure 3:
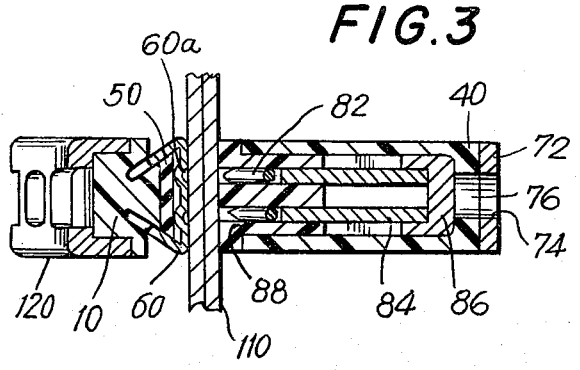
FIG. 3 is a sectional view taken along the line 3—3 in FIG. 2.

Referring now to FIG. 1, staple holding assembly 20, which includes housing 40 and two parallel rows of staple containing apertures 78a and 78b, is pivotally mounted adjacent one end of anvil support member 10 by mounting pin 42. As best seen in FIG. 3, anvil member 60 is retained on anvil support member 10 by being fitted over an outwardly flared rail portion of anvil support member 10. Resilient means 50, such as a strip of elastic material, is provided between anvil member 60 and anvil support member 10 to allow anvil member 60 to displace toward anvil support member 10 in the event that the instrument is inadvertently placed around too much tissue as discussed in greater detail below. Biasing means such as an internally located spring (not shown)

is provided for resiliently biasing staple holding assembly 20 so that it normally pivots away from anvil member 60 as shown in FIG. 1. When thus pivoted apart, a V-shaped space 80 is defined between anvil member 60 and staple holding assembly 20.

Figure 2:
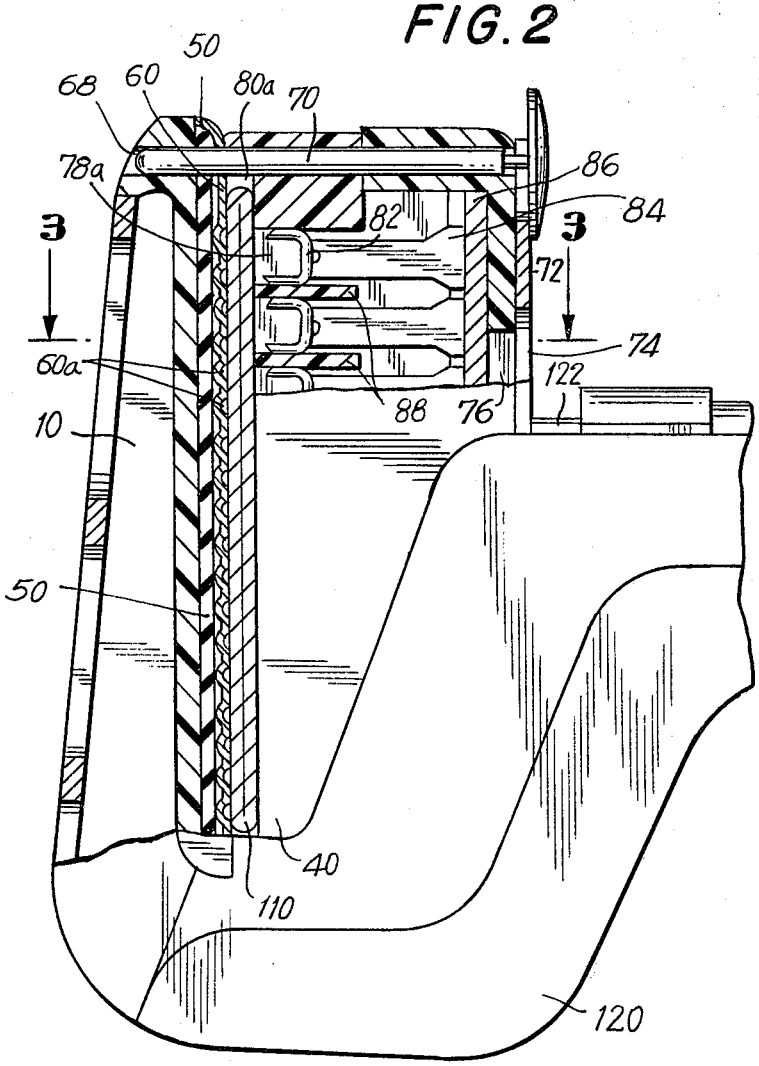
FIG. 2 is an enlarged elevational sectional view of a part of the surgical stapling assembly of FIG. 1 showing the surgical stapling assembly mounted in an actuator assembly, showing tissue clamped between the anvil member and the staple holding assembly ready for stapling, and showing one embodiment of the resilient means of the present invention mounted between the anvil support member and the anvil member.

The stapling assembly shown in FIG. 1 is adapted for mounting in the distal end of actuator assembly 120 as shown in FIGS. 2 and 3. The stapling assembly is mounted in actuator assembly 120 by means of a rigid connection between anvil support member 10 and the adjacent portion of the frame of the actuator assembly. When the stapling assembly is thus mounted in actuator assembly 120, the actuator assembly controls the pivoting of staple holding assembly 20 about the axis of pin 42. In particular, actuator assembly 120 can be operated to pivot staple holding assembly 20 into substantially parallel spaced relation to anvil 60 as shown in FIGS. 2 and 3. Suitable actuator assemblies are shown in above-mentioned U.S. patent application Ser. Nos. 188,691 and 267,080. Typically at least the staple holding assembly is manufactured as a disposable item which is discarded after the staples initially contained in it have been driven as described below. In this way, all difficulty and expense of cleaning, sterilizing, and reloading the stapling assembly for reuse are completely avoided. The stapling assembly may be either integral with actuator assembly 120, in which case the actuator assembly is also disposable after a single use, or the stapling assembly may be removably mounted in a permanent and reusable actuator assembly. When the staple holding assembly 20 is pivoted parallel to anvil member 60, spacer member 46, which projects from housing 40 on the side of the housing remote from pin 42, contacts anvil member 60 to help maintain the general parallelism and fixed predetermined spacing 80a between staple holding assembly 20 and anvil member 60.

Another preferred feature of the stapling assembly is an alignment-maintaining structure which includes pin 70, leaf spring 72 and bore 68. Pin 70 is slidably mounted in a bore through housing 40 on the side of the housing remote from pin 42. When staple holding assembly 20 is pivoted away from anvil member 60 as shown in FIG. 1, pin 70 is maintained in a retracted position within housing 40 by leaf spring 72 (or other suitable biasing means) so that the pin does not obstruct opening 80 and thereby present an obstacle to tissue 110 being placed in or removed from space 80. As further shown in FIG. 1, leaf spring 72 contains an elongated slot 74 which is in alignment with a corresponding elongated slot 76 in the adjacent side of housing 40 as shown in FIG. 3. A longitudinal pusher member 122 shown in FIG. 2 and associated with actuator assembly 120 passes through slots 74 and 76 when the stapling assembly is placed in the actuator assembly and the actuator assembly is operated as described below.

When actuator 120 is operated to pivot staple holding assembly 20 toward anvil member 60, a distally directed clamping force is applied to the proximal surface of leaf spring 72. This causes leaf spring 72 to deflect toward housing 40, and also causes staple holding assembly 20 to pivot toward anvil member 60. Deflection of leaf spring 72 advances pin 70 through the bore in housing 40 and then through a hole in anvil member 60 which communicates and is in registry with bore 68 in anvil support member 10. Thus, when anvil member 60 and staple holding assembly 20 are in substantially parallel spaced relation, pin 70 extends through housing 40, anvil member 60 and anvil support member 10 to help keep staple holding assembly 20 and, accordingly, staple containing apertures 78a and 78b aligned with anvil member 60 during stapling of the clamped tissue.

Each staple containing aperture 78a, 78b is provided with a single staple 82. When staple holding assembly 20 is pivoted into substantially parallel spaced relation to anvil member 60, each parallel row of apertures 78a and 78b is aligned with a respective one of two parallel rows of anvil pockets 60a in anvil member 60 so that each anvil pocket in the associated row of anvil pockets is opposite each point of the staple in the aperture aligned therewith. Maintenance of this alignment is enhanced during stapling when the previously discussed, preferred alignment-maintaining assembly is included in the stapling assembly.

Behind each staple 82 in staple holding assembly 20 is a staple pusher 84, which is slidably mounted in staple housing 40. As shown in FIGS. 2 and 3, inwardly extending portions 88 of housing 40 define channels which maintain each staple pusher 84 in registry with the associated staple 82. The proximal ends of staple pushers 84 all contact transverse pusher member 86, which is also slidably mounted in staple housing 40. Elements 84 and 86 thus comprise the staple driving means in staple holding assembly 20. Access to this staple driving means is through the elongated slot 76 in housing 40 which was previously discussed in connection with the preferred alignment-maintaining means.

Considering resilient means 50 now in more detail, the purpose of this element is to allow anvil member 60 to move away from staple holding assembly 20 and toward anvil support member 10 in the event that too much tissue is clamped in the instrument. The amount of this motion of anvil member 60 is great enough to reduce the pressure on the tissue, but not so great that the ends of the staple legs cannot reach anvil member 60 to be crimped by the anvil when the staples are driven. Accordingly, the maximum displacement of anvil member 60 allowed by resilient means 50 is such that the distance between the staple holding assembly and the maximally displaced anvil member is less than the length of the legs of the uncrimped surgical staples. For example, in apparatus in which the length of the uncrimped staple legs is about 0.189 inch and in which the distance between the parallel anvil member and staple holding assembly with no displacement of the anvil member is about 0.09 inch, the maximum displacement of the anvil member relative to the staple holding assembly is up to about an additional 0.04 inch.

The resiliency of resilient means 50 is preferably such that anvil member 60 is not displaced during clamping of the tissue when the stapling assembly is not overloaded with tissue. Resilient means 50 therefore does not come into play unless the stapling assembly is overloaded and the operator clamps the tissue despite the overloading. It is to be understood, however, that anvil member 60 may be temporarily displaced by a small amount in the direction of application of the staple driving force to the staple driving means during crimping of the staples.

Figure 4:
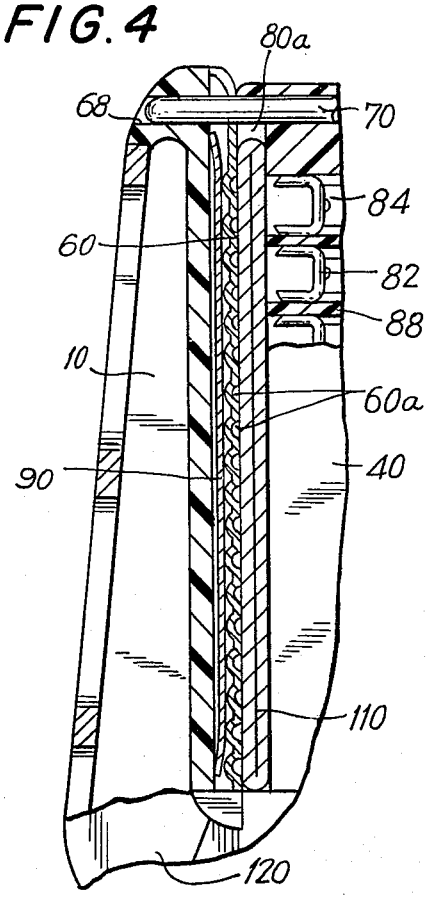
FIG. 4 is a view similar to FIG. 2 showing an alternative embodiment of the resilient means of the present invention mounted between the anvil member and the anvil support member.

As mentioned above, resilient means 50 may be a strip of elastic material as shown in FIGS. 2 and 3. Alternatively the resilient means may be a plurality of springs, a single leaf spring 90 as the alternative embodiment shown in FIG. 4, or any equivalent resilient means. (Except for the different construction of the resilient means, the embodiment of FIG. 4 may be identical to the embodiment of FIGS. 1–3.) When a strip of elastic material is employed, it is preferably of a length and width substantially equal to the corresponding dimensions of the anvil member. As the elastic material, synthetic rubber, natural rubber or the like may be employed. When a single leaf spring 90 is employed as shown in FIG. 4, it preferably has a length substantially equal to the length of the anvil member. The spring or springs may be made of metal or plastic. If a plastic spring is employed, it may be formed as an integral part of a plastic anvil support member 10.

Anvil member 60, pin 10, leaf spring 72, staples 82, staple pushers 84 and transverse pusher member 86 are typically made of metal. The remaining elements of the surgical stapling assembly are typically made of plastic in order to make the assembly more economically disposable.

Considering now the operation of the stapling assemblies of FIGS. 1 through 4, the stapling assembly is first inserted in actuator assembly 120 as described above. The stapling assembly is then positioned so that the tissue 110 to be stapled is located in space 80. Thereafter, actuator assembly 120 is operated to pivot staple holding assembly 20 into substantially parallel spaced relation to anvil member 60 to clamp tissue 110 between the opposing surfaces of the staple holding assembly and anvil. Ideally, the operator has placed the instrument around the correct amount of tissue so that staple holding assembly 20 can be brought into substantially parallel spaced relationship with anvil member 60 with little or no compression of resilient means 50 or 90. If, however, the operator has inadvertently placed the instrument around too much tissue, resilient means 50 or 90 compresses in the general direction of the clamping force and allows anvil member 60 to move closer to anvil support member 10. This increases the distance between anvil member 60 and staple holding assembly 20 to relieve the pressure on and reduce the chance of injury to the tissue.

Spring 72 is deflected during the clamping operation, thereby advancing pin 70 into bore 68 and insuring the alignment of the two parallel rows of staple containing apertures 78a and 78b with the two associated parallel rows of anvil pockets 60a. Actuator assembly 120 is then further operated to exert a staple driving force on transverse pusher member 86 by means of longitudinal pusher member 122 inserted through slot 74 in spring 72 and slot 76 in housing 40. Movement of transverse pusher member 86 toward anvil member 60 simultaneously moves staple pushers 84 in the same direction. This movement pushes staples 82 through the tissue 110 and into contact with anvil member 60. Resilient means 50 or 90 maintains the displaced anvil member 60 at a distance from the staple holder 20 during stapling which is less than the length of the uncrimped staple legs. Accordingly, upon continued application of the staple driving force, the points of the staples are bent inwards by contact with anvil pockets 60a, forming finished staples in tissue 110. Application of the staple driving force is then discontinued, actuator assembly 120 is operated to release the clamping force on the stapled tissue, and the instrument is removed from the stapled tissue.

Although the invention has been described with reference to the illustrative embodiments shown in FIGS. 1 through 4, the invention generally includes within its scope an improved surgical stapling assembly for use in a surgical stapler apparatus for forming a plurality of surgical staples in body tissue wherein the stapling assembly is of the type including a staple holding assembly disposed on one side of the tissue to be stapled, an anvil member disposed opposite and aligned with the staple holding assembly on the other side of the tissue to be stapled, and means mounting the staple holding assembly and anvil member for movement towards a midpoint to clamp the tissue therebetween. In other preferred embodiments, either the staple holding assembly or the anvil member may be fixed relative to the other and the other mounted for movement to clamp the tissue therebetween. The staple holding assembly contains a plurality of surgical staples and includes staple driving means for driving the staples from the staple holding assembly so that the ends of the staples pass through the tissue and are crimped against the anvil member.

The improvement comprises mounting the anvil member on resilient means so that if the stapling assembly is overloaded with too much tissue, the anvil member can move away from the staple holding assembly by an amount sufficient to reduce the pressure on the tissue, the total distance between the anvil member and the staple holding assembly remaining less than the length of the legs of the uncrimped staples. In one preferred embodiment, the staple holding assembly and the resiliently mounted anvil member are separate, disposable units which together comprise the surgical stapling assembly.

Examples of other types of surgical staplers to which the invention is applicable include the non-pivoting linear closure surgical staplers shown in commonly assigned U.S. Pat. No. 3,494,533, the linear anastomosis surgical staplers shown in commonly assigned U.S. Pat. No. 3,499,591, and the circular anastomosis surgical staplers shown in commonly assigned copending application Ser. No. 138,878, filed Apr. 10, 1980. In any of these types of instruments, the anvil member may be mounted on resilient means in accordance with the principles of this invention to reduce the possibility that excessive pressure may be applied to the clamped tissue. In some of these instruments the tissue gap is variable by the operator rather than fixed by the design of the instrument, but the present invention may still be useful to prevent excessive pressure on the tissue.

It will be understood that the particular embodiments described above are only illustrative of the principles of the invention, and that various modifications can be made by those skilled in the art without departing from the scope and spirit of the invention. For example, various types of resilient means can be employed as illustrated by the elastic strip 50 or mounting spring 90 described above.

I claim:

1. A surgical stapling assembly for use with an actuator assembly for simultaneously forming a plurality of surgical staples in body tissue comprising an anvil support member, resilient means mounted on the anvil support member, an anvil member mounted on the resilient means, a staple holding assembly, and means mounting the staple holding assembly relative to the anvil support member for movement into spaced relation to the anvil member to clamp tissue inserted therebetween, said staple holding assembly containing a plurality of surgical staples and including staple driving means for simultaneously driving all of the staples from the staple holding assembly through the clamped tissue and then into contact with the anvil member to crimp the staples, said anvil member being mounted on said resilient means so that when the stapling assembly is overloaded with tissue and the anvil member and staple holding assembly are moved into spaced relation, the anvil member is displaced, relative to the staple holding assembly, a distance sufficient to reduce pressure on the overloaded tissue, said displacement being such that the distance between the staple holding assembly and the displaced anvil member is less than the length of the legs of the uncrimped surgical staples.

2. The surgical stapling assembly of claim 1 wherein the staple holding assembly is pivotally mounted adjacent one end of the anvil support member for pivotal movement into predetermined spaced relation to the anvil member.

3. The surgical stapling assembly of claim 2 wherein the distance between the non-displaced anvil member and the staple holding assembly in spaced relation thereto is about 0.09 inch and the maximum displacement of the anvil member relative to the staple holding assembly when the stapling assembly is overloaded is up to about an additional 0.04 inch.

4. The surgical stapling assembly of claim 1, 2 or 3 wherein the resilient means is a strip of elastic material.

5. The surgical stapling assembly of claim 4 wherein the strip of elastic material has a length and width substantially equal to the corresponding dimensions of the anvil member.

6. The surgical stapling assembly of claim 1, 2 or 3 wherein the resilient means is a leaf spring having a length substantially equal to the length of the anvil member.

7. In a surgical stapling assembly for use in a surgical stapler apparatus for forming a plurality of surgical staples in body tissue wherein the stapling assembly is of the type including a staple holding assembly disposed on one side of the tissue to be stapled, an anvil member disposed opposite and aligned with the staple holding assembly on the other side of the tissue to be stapled, and means mounting the staple holding assembly and anvil member for movement toward a midpoint to clamp the tissue therebetween, said staple holding assembly containing a plurality of surgical staples and including staple driving means for driving the staples from the staple holding assembly so that the ends of the staples pass through the tissue and are crimped against the anvil member, the improvement comprising mounting the anvil member on resilient means so that when the surgical stapling assembly is overloaded with tissue with anvil member is displaced, relative to the staple holding assembly, a distance sufficient to reduce pressure on the overloaded tissue and less than the length of the legs of the uncrimped staples.

8. The surgical stapling assembly of claim 7 wherein the staple holding assembly is fixed relative to the anvil member and including means mounting the anvil member for movement towards the staple holding assembly to clamp the tissue therebetween.

9. The surgical stapling assembly of claim 7 wherein the anvil member is fixed relative to the staple holding assembly and including means mounting the staple holding assembly for movement towards the anvil member to clamp the tissue therebetween.

10. The surgical stapling assembly of claim 7, 8 or 9 wherein the staple holding assembly and the resiliently mounted anvil are separate, disposable units.

* * * * *

UNITED STATES PATENT AND TRADEMARK OFFICE
CERTIFICATE OF CORRECTION

PATENT NO. : 4,415,112
DATED : November 15, 1983
INVENTOR(S) : David T. Green

It is certified that error appears in the above—identified patent and that said Letters Patent is hereby corrected as shown below:

Column | Line
--- | ---
8 | 16     "with" should be --the--

Signed and Sealed this

Twenty-sixth Day of February 1985

[SEAL]

Attest:

DONALD J. QUIGG

Attesting Officer     Acting Commissioner of Patents and Trademarks